(12) United States Patent
Mamiya

(10) Patent No.: US 11,944,841 B2
(45) Date of Patent: Apr. 2, 2024

(54) LIGHT-IRRADIATION-DEVICE DELIVERY APPARATUS AND PHOTOTHERAPY METHOD

(71) Applicant: OLYMPUS CORPORATION, Tokyo (JP)

(72) Inventor: Tomohiko Mamiya, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 544 days.

(21) Appl. No.: 17/060,691

(22) Filed: Oct. 1, 2020

(65) Prior Publication Data
US 2021/0016102 A1    Jan. 21, 2021

Related U.S. Application Data

(63) Continuation of application No. PCT/JP2018/032738, filed on Sep. 4, 2018.

(51) Int. Cl.
*A61N 5/06*    (2006.01)

(52) U.S. Cl.
CPC ........... *A61N 5/062* (2013.01); *A61N 5/0601* (2013.01); *A61N 2005/0609* (2013.01);
(Continued)

(58) Field of Classification Search
CPC ................. A61N 5/062; A61N 5/0601; A61N 2005/0609; A61N 2005/0612; A61N 2005/063; A61N 2005/0659
See application file for complete search history.

(56) References Cited

U.S. PATENT DOCUMENTS

| 6,152,918 A * | 11/2000 | Padilla ................... A61B 18/22 |
| | | 606/7 |
| 2005/0285928 A1 | 12/2005 | Broome et al. |

(Continued)

FOREIGN PATENT DOCUMENTS

| AU | 2013201683 A1 | 10/2013 |
| AU | 2017248500 A1 | 11/2017 |

(Continued)

OTHER PUBLICATIONS

International Search Report dated Dec. 11, 2018 issued in PCT/JP2018/032738.

(Continued)

*Primary Examiner* — Ahmed M Farah
*Assistant Examiner* — Naveed R. Kolia
(74) *Attorney, Agent, or Firm* — Scully, Scott, Murphy & Presser, P.C.

(57) ABSTRACT

A light-irradiation-device delivery apparatus includes: a metal needle tube having a longitudinal axis, a side hole, which penetrates from an inner circumferential surface to an outer circumferential surface, and a blade surface at a distal end thereof; an optical fiber that is accommodated inside the needle tube, the optical fiber including a core allowing light to propagate, a clad covering an outer circumferential surface of the core, and an emission area provided at a distal-end section of the optical fiber; and a positioning member that positions the emission area between a distal end and a proximal end of the needle tube in the longitudinal-axis direction. The distal end of the optical fiber is positioned in an interior space of the needle tube in a state where the emission area is positioned between the distal end and the proximal end of the side hole.

20 Claims, 17 Drawing Sheets

(52) U.S. Cl.
CPC ............... *A61N 2005/0612* (2013.01); *A61N 2005/063* (2013.01); *A61N 2005/0659* (2013.01)

(56) References Cited

U.S. PATENT DOCUMENTS

| | | | |
|---|---|---|---|
| 2006/0217695 A1 | 9/2006 | DeBenedictis et al. | |
| 2012/0010558 A1 | 1/2012 | Kobayashi et al. | |
| 2013/0253266 A1* | 9/2013 | Dextradeur | A61M 25/007 600/104 |
| 2013/0261368 A1* | 10/2013 | Schwartz | A61B 18/06 607/2 |
| 2013/0336995 A1 | 12/2013 | Kobayashi et al. | |
| 2014/0120119 A1 | 5/2014 | Kobayashi et al. | |
| 2014/0163371 A1* | 6/2014 | Matsui | A61B 8/12 600/439 |
| 2015/0031956 A1 | 1/2015 | Dextradeur et al. | |
| 2016/0015829 A1 | 1/2016 | Kobayashi et al. | |
| 2017/0079628 A1 | 3/2017 | Mamiya | |
| 2020/0049874 A1 | 2/2020 | Eckardt | |
| 2020/0085950 A1 | 3/2020 | Kobayashi et al. | |
| 2020/0095331 A1 | 3/2020 | Kobayashi et al. | |

FOREIGN PATENT DOCUMENTS

| | | |
|---|---|---|
| CA | 2809948 A1 | 9/2013 |
| EP | 2641528 A1 | 9/2013 |
| EP | 3266382 A1 | 1/2018 |
| JP | 2006-167046 A | 6/2006 |
| JP | 2008-148951 A | 7/2008 |
| JP | 2008-529682 A | 8/2008 |
| JP | 2013-192955 A | 9/2013 |
| JP | 2014-523907 A | 9/2014 |
| JP | 2016-168259 A | 9/2016 |
| JP | 5985131 B1 | 9/2016 |
| WO | WO 2006/088993 A2 | 8/2006 |
| WO | WO 2006/090596 A1 | 8/2006 |
| WO | WO 2013/009475 A1 | 1/2013 |
| WO | WO 2020/049632 A1 | 3/2020 |

OTHER PUBLICATIONS

"The future of cancer treatment aimed at by photoimmunotherapy", Cancer Plus, Qlife, Inc., Retrieved from the Internet, URL:https://cancer.qlife.jp/immuno/immuno_feature/article10706.html.

"Cylindrical Diffuser, Medlight", Opto Science, Inc., Retrieved from the Internet in Apr. 2018, URL:https://www.optoscience.com/maker/medlight/lineup/cylindrical_diffuser.html.

"Near-infrared rays kill cancer cells in one day and cure metastatic cancer", Innovation-inspired digital media mugendai, Retrieved from the Internet, URL:https://www.mugendai-web.jp/archives/6080.

* cited by examiner

LIGHT-IRRADIATION-DEVICE DELIVERY APPARATUS AND PHOTOTHERAPY METHOD

CROSS-REFERENCE TO RELATED APPLICATIONS

This is a continuation of International Application PCT/JP2018/032738, with an international filing date of Sep. 4, 2018, which is hereby incorporated by reference herein in its entirety.

TECHNICAL FIELD

The present invention relates to a light-irradiation-device delivery apparatus and a phototherapy method.

BACKGROUND ART

There is a known technique in which, after injection of a drug that accumulates specifically in a cancer cell and that reacts to near infrared light to induce death of the cancer cell, near infrared light is radiated onto the cancer cell by means of an optical fiber inserted into the body (for example, see PTL 1).

CITATION LIST

Patent Literature

{PTL 1} Japanese Translation of PCT International Application, Publication No. 2014-523907

SUMMARY OF INVENTION

One aspect of the present invention is directed to a light-irradiation-device delivery apparatus comprising: a metal needle tube that has a longitudinal axis and that has a side hole and a blade surface at a distal end thereof, the side hole penetrating from an inner circumferential surface to an outer circumferential surface; an optical fiber that is accommodated inside the needle tube, the optical fiber comprising a core allowing light to propagate, a clad covering an outer circumferential surface of the core, and an emission area provided at a distal-end section of the optical fiber; and a positioning member that positions the emission area between a distal end and a proximal end of the side hole in the longitudinal-axis direction of the needle tube, the positioning member having a surface that is provided at a position closer to the distal end than the side hole of the needle tube is and against which a distal end of the optical fiber abuts, wherein the distal end of the optical fiber is positioned in an interior space of the needle tube in a state in which the emission area is positioned between the distal end and the proximal end of the side hole.

Another aspect of the present invention is directed to a phototherapy method including: introducing an ultrasound endoscope into a digestive tract; visualizing an irradiation target site in a body by the ultrasound endoscope introduced into the digestive tract; puncturing a vicinity of the irradiation target site with a needle tube protruding from a distal-end section of the ultrasound endoscope introduced into the digestive tract; and radiating light emitted from an optical fiber inside the needle tube onto the irradiation target site through a side hole formed in the needle tube that has punctured the vicinity of the irradiation target site.

Another aspect of the present invention is directed to a light-irradiation-device delivery apparatus comprising: a metal needle tube that has a longitudinal axis and that has a side hole and a blade surface at a distal end thereof, the side hole penetrating from an inner circumferential surface to an outer circumferential surface; an optical fiber that is accommodated inside the needle tube, the optical fiber comprising a core allowing light to propagate, a clad covering an outer circumferential surface of the core, and an emission area provided at a distal-end section of the optical fiber; a sheath that accommodates the needle tube so as to be movable along the longitudinal axis; a main body that is fixed to a proximal end of the sheath; and a needle slider that is supported so as to be movable in a direction along the longitudinal axis with respect to the main body and to which a proximal end of the needle tube is fixed, wherein the needle slider comprises a positioning member that detachably fixes the optical fiber and that positions the emission area between a distal end and a proximal end of the side hole in the longitudinal-axis direction of the needle tube; and the distal end of the optical fiber is positioned in an interior space of the needle tube in a state in which the emission area is positioned between the distal end and the proximal end of the side hole.

DESCRIPTION OF EMBODIMENT

A light-irradiation-device delivery apparatus 100 and a phototherapy method according to one embodiment of the present invention will be described below with reference to the drawings.

Figure 1:
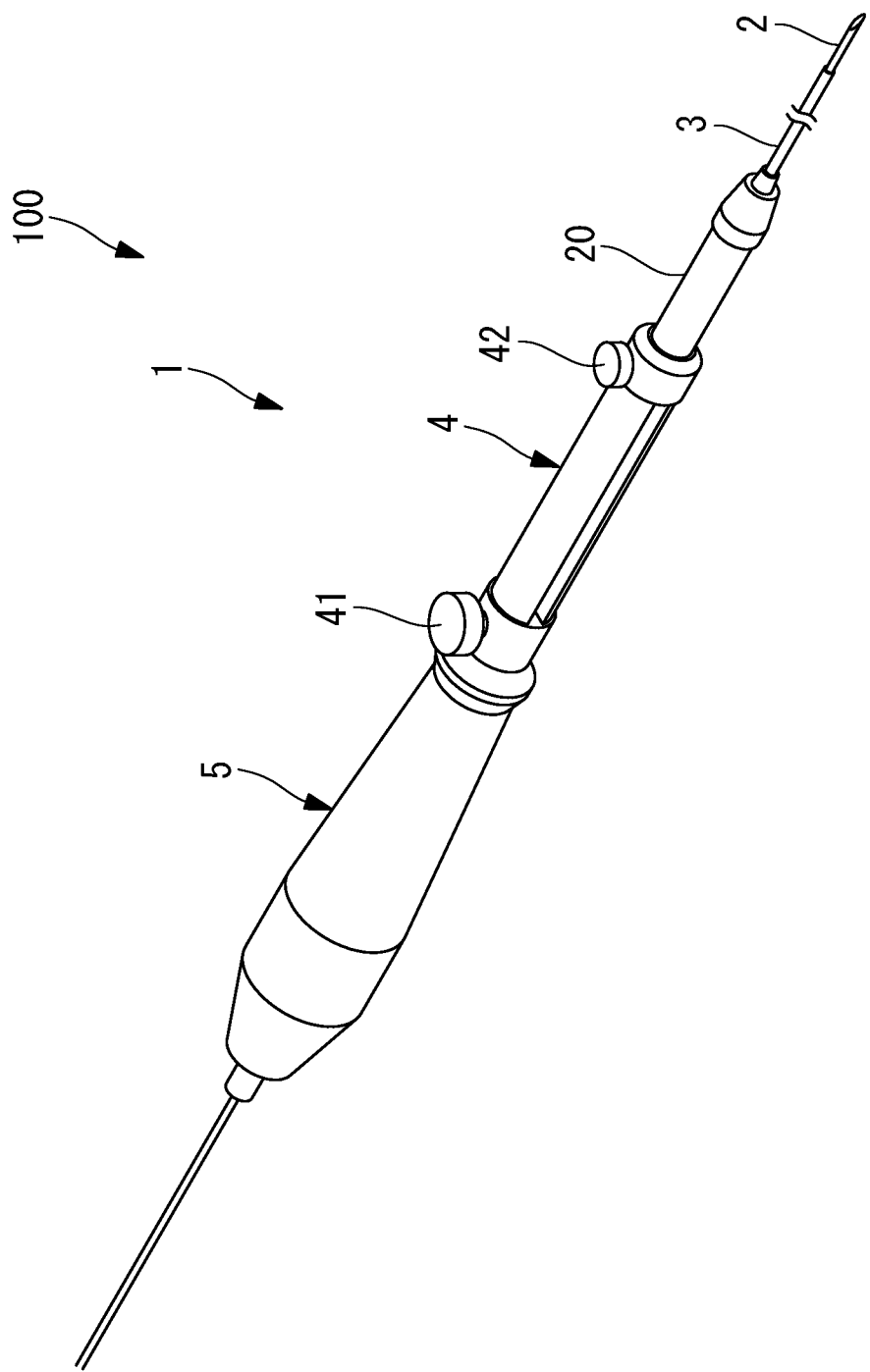
FIG. 1 is a view showing the overall configuration of a light-irradiation-device delivery apparatus according to one embodiment of the present invention.
Figure 2:
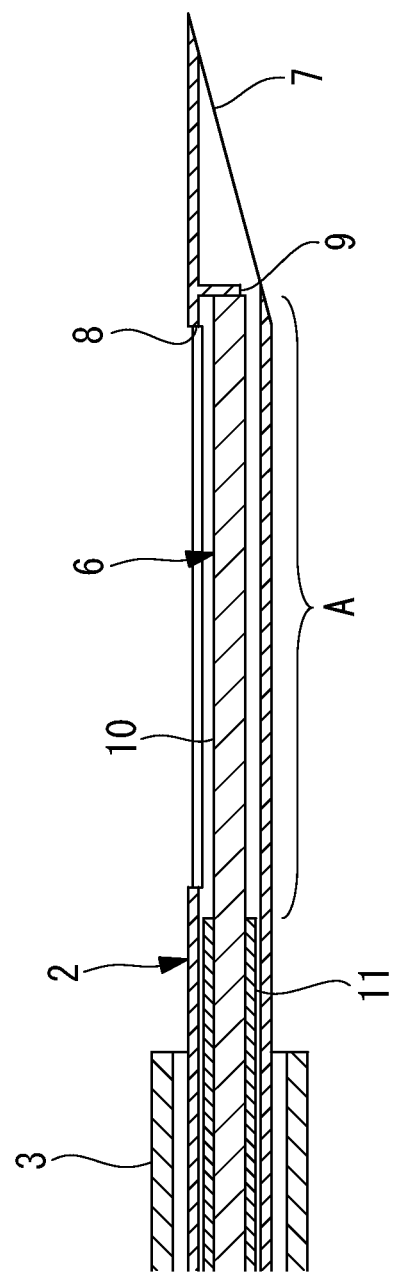
FIG. 2 is a longitudinal sectional view showing a needle tube provided in the light-irradiation-device delivery apparatus shown in FIG. 1.

As shown in FIGS. 1 and 2, the light-irradiation-device delivery apparatus 100 of this embodiment includes: a puncture device 1 that can be accommodated in an ultrasound endoscope 200; and an optical fiber 6 that is accommodated in the puncture device 1.

The puncture device 1 includes: a metal tubular needle tube 2 that has a longitudinal axis; a flexible sheath 3 that accommodates the needle tube 2 so as to be movable in the longitudinal-axis direction; an attachment adaptor 20 that can be attached to a channel in the ultrasound endoscope 200; a main body 4 to which a proximal end of the sheath 3 is fixed and that is supported so as to be movable in the direction along the longitudinal axis with respect to the attachment adaptor 20; and a needle slider 5 that is supported so as to be movable in the direction along the longitudinal axis with respect to the main body 4.

A proximal end of the needle tube 2 is fixed to a proximal end of the needle slider 5.

The main body 4 is provided with: a stopper 41 that adjustably defines a forward position of the needle slider 5 with respect to the main body 4; and a fixing screw 42 that fixes the main body 4 at an arbitrary position with respect to the attachment adaptor 20.

Figure 3:
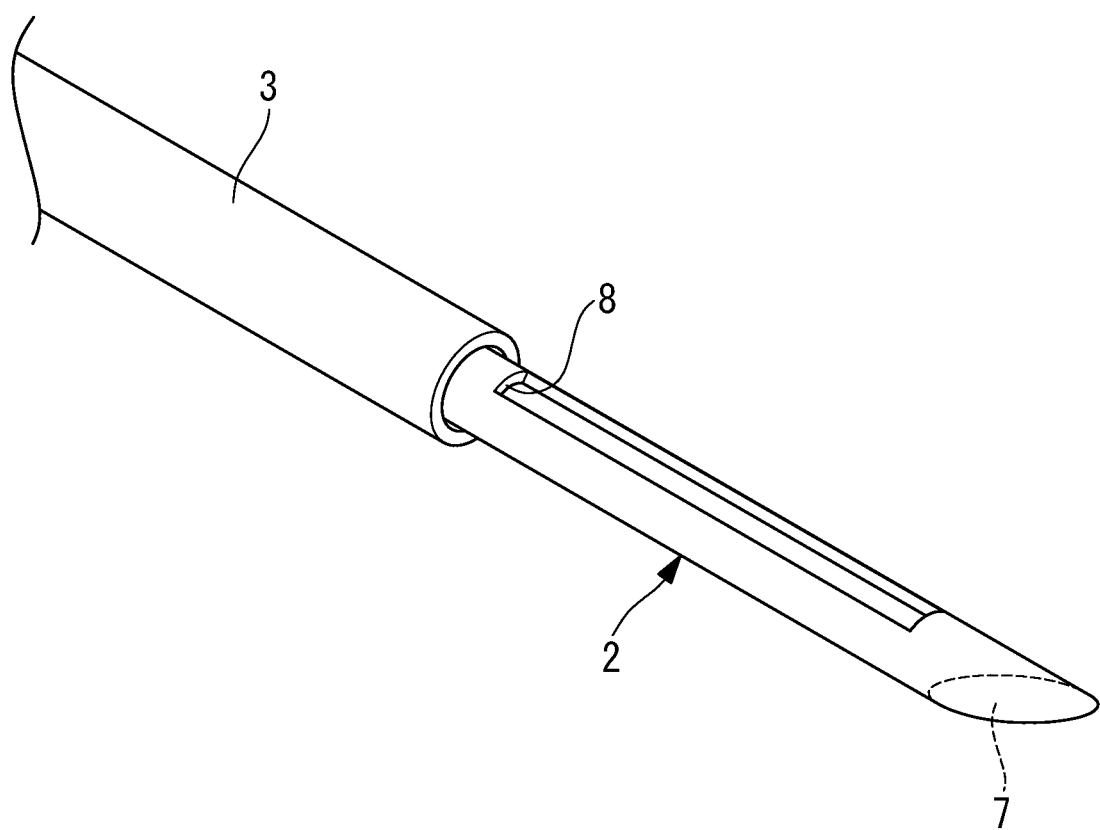
FIG. 3 is a perspective view of the needle tube shown in FIG. 2.

As shown in FIG. 2, the needle tube 2 is formed in a cylindrical shape and has: a blade surface 7 that has a shape obtained by diagonally cutting a distal end thereof in a plane intersecting the longitudinal axis; and a side hole 8 penetrating in a radial direction over a predetermined range that is closer to the proximal end than a proximal end of the blade surface 7 is and that extends in the longitudinal-axis direction. As shown in FIG. 3, the side hole 8 is, for example, a slit that penetrates a circumferential section of the needle tube 2 in a straight-line manner in the longitudinal-axis direction with a fixed opening width.

The proximal end of the needle tube 2 is fixed to the proximal end of the needle slider 5, and the needle tube 2 is made to advance and retreat in the longitudinal-axis direction with respect to the sheath 3 through movement of the needle slider 5 in the longitudinal-axis direction with respect to the main body 4.

The proximal end of the sheath 3 is fixed to the main body 4, and the sheath 3, which is fixed to the main body 4, is made to advance and retreat in the longitudinal-axis direction integrally with the needle tube 2, which is fixed to the needle slider 5, through movement of the main body 4 in the longitudinal-axis direction with respect to the attachment adaptor 20.

Figure 4:
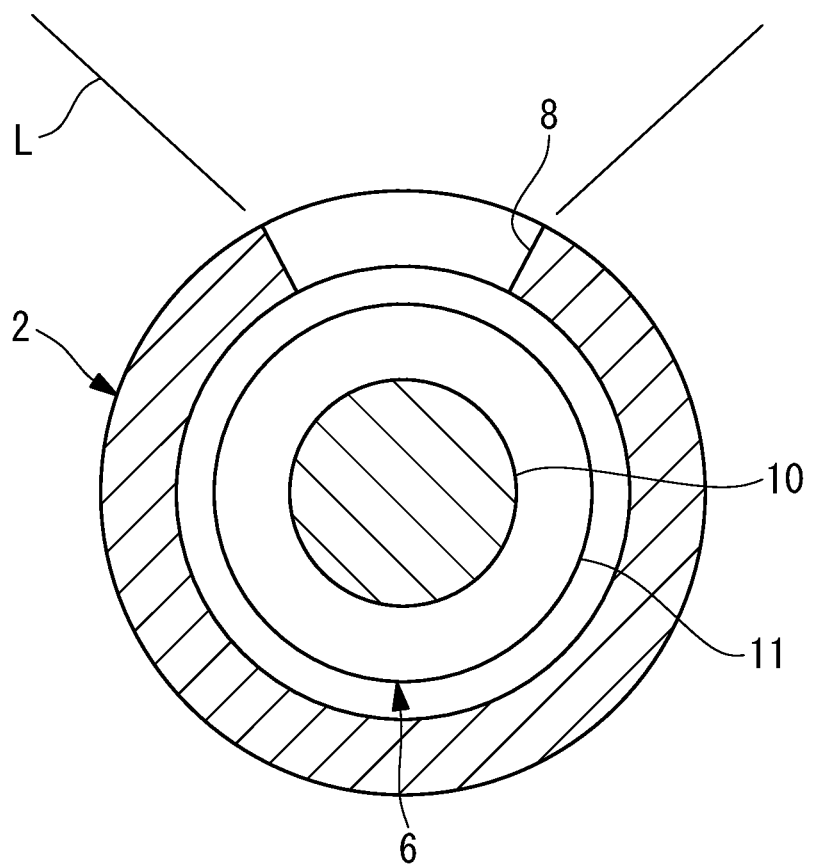
FIG. 4 is a cross-sectional view of the needle tube shown in FIG. 2 and an optical fiber accommodated inside the needle tube.

As shown in FIG. 4, the width dimension of the side hole 8 in the circumferential direction is set so as to be less than the outer-diameter dimension of a core 10 of the optical fiber 6, which is accommodated inside the needle tube 2.

Furthermore, as shown in FIG. 2, a protrusion (positioning member) 9 that protrudes radially inward at a position closer to the distal end than the side hole 8 is and against which a distal end of the optical fiber 6, which is accommodated inside the needle tube 2, is made to abut is provided on an inner surface of the needle tube 2.

As shown in FIG. 2, the optical fiber 6 includes the core 10, through which light propagates, and a clad 11 that covers an outer circumferential surface of the core 10, and also includes, at a distal-end section of the optical fiber 6, an emission area A where the core 10 is exposed by partially peeling off the clad 11. The emission area A is formed to have a length equal to or greater than the longitudinal dimension of the side hole 8. Accordingly, when the distal end of the optical fiber 6 is moved forward until it abuts against the protrusion 9, the emission area A is disposed at a position so as to overlap, in the longitudinal direction, over the entire length of the side hole 8 of the needle tube 2.

Specifically, a distal end of the emission area A is positioned at the same position as a distal end of the side hole 8 or at a position closer to a distal end of the needle tube 2 than the distal end of the side hole 8 is, and a proximal end of the emission area A is positioned at the same position as a proximal end of the side hole 8 or at a position closer to the proximal end of the needle tube 2 than the proximal end of the side hole 8 is.

A light source (not shown) that emits near infrared light L is connected to a proximal end of the optical fiber 6.

The phototherapy method using the light-irradiation-device delivery apparatus 100 of this embodiment will be described below.

A description will be given below of an example case in which the phototherapy method of this embodiment is applied to a cancer cell present in the pancreas.

Figure 5:
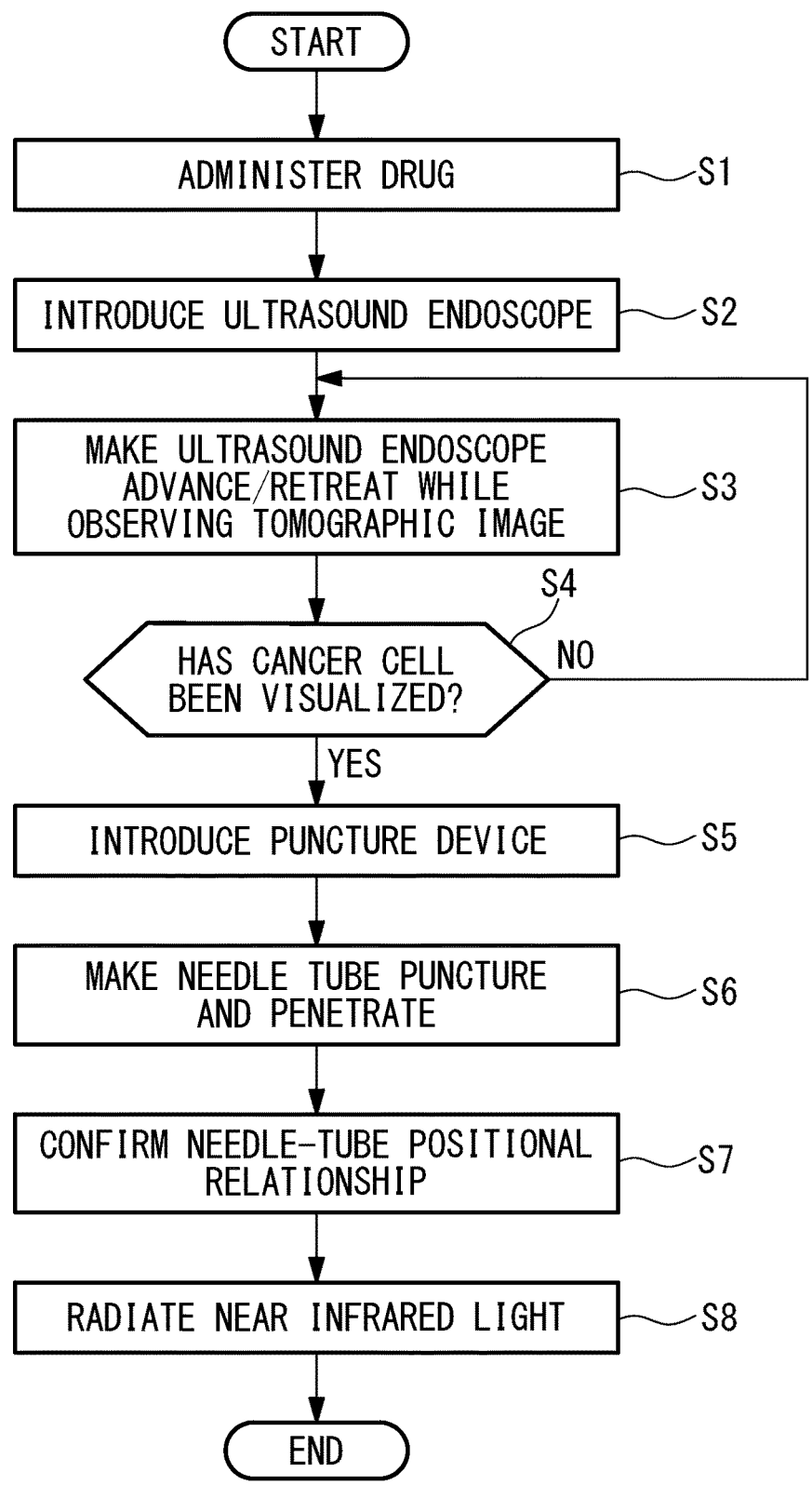
FIG. 5 is a flowchart for explaining a phototherapy method according to the embodiment of the present invention.

As shown in FIG. 5, in the phototherapy method of this embodiment, a drug that reacts to the near infrared light L to damage a cancer cell (irradiation target site) X through heat generation etc., thereby inducing cell death of the cancer cell, is administered to a patient in advance (Step S1), and the ultrasound endoscope 200 is introduced into a digestive tract Y such as the stomach or the duodenum (Step S2).

The ultrasound endoscope 200 is made to advance or retreat while observing the cancer cell X present in a tomographic image of an organ, for example, the pancreas, adjacent to the digestive tract Y by means of the ultrasound endoscope 200 (Step S3), and the ultrasound endoscope 200 is disposed at a position where the cancer cell X can be visualized (Step S4).

Figure 6:
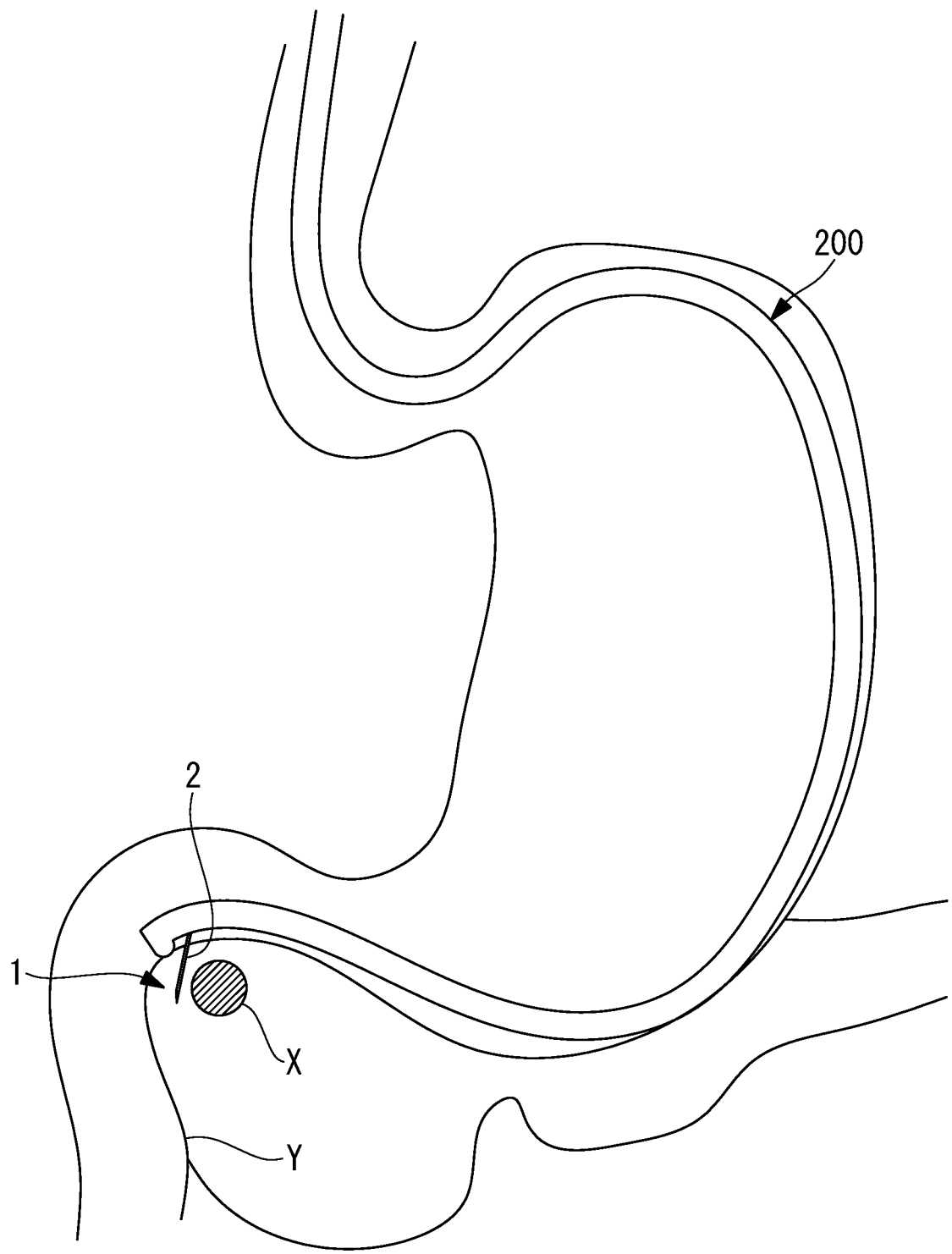
FIG. 6 is a view showing a state in which the needle tube punctures a digestive tract, in the phototherapy method shown in FIG. 5.

When the ultrasound endoscope 200 is inserted up to the position where the cancer cell X can be visualized, the puncture device 1 is made to protrude, via the channel provided in the ultrasound endoscope 200, from a distal end of the channel in the ultrasound endoscope 200 (Step S5). At this time, the attachment adaptor 20 is attached to the channel in the ultrasound endoscope 200. Then, as shown in FIG. 6, the needle tube 2 is made to protrude from a distal-end opening of the channel in the ultrasound endoscope 200, the needle tube 2 punctures the wall of the digestive tract Y, and the needle tube 2 is made to penetrate the wall of the digestive tract Y and punctures the pancreas adjacent to the digestive tract Y (Step S6).

Figure 7:
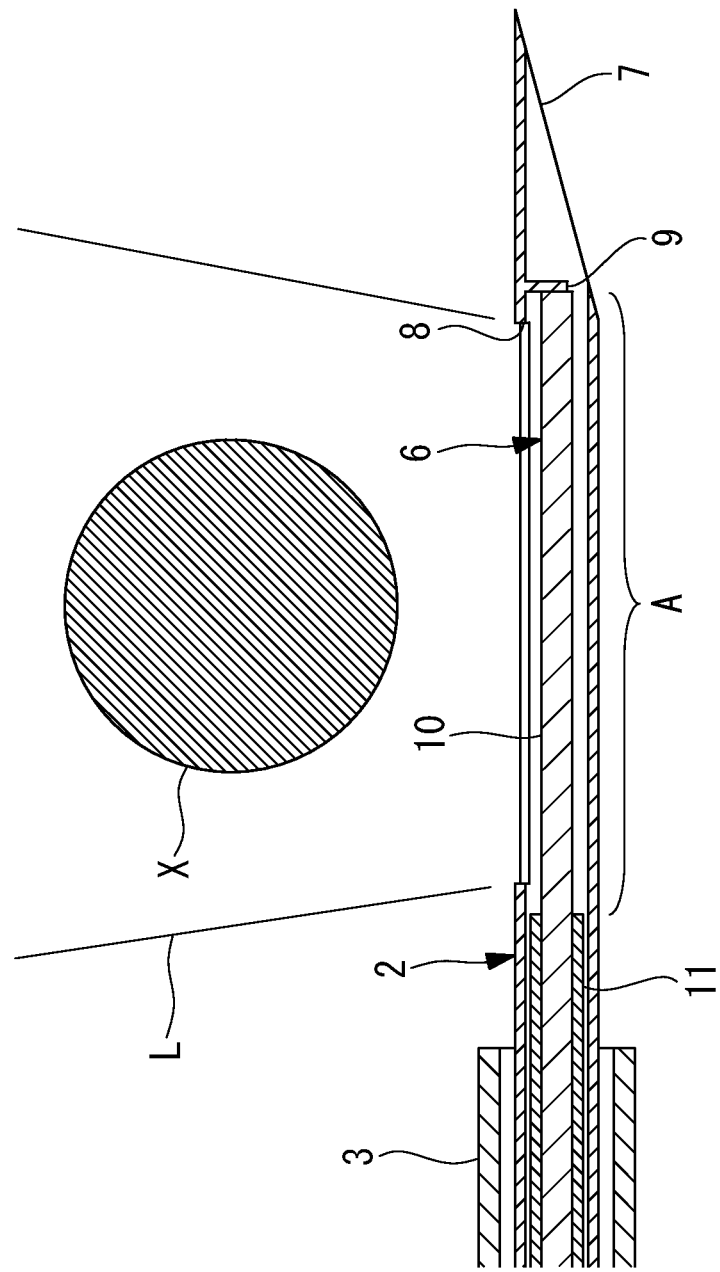
FIG. 7 is a view showing a state in which a side hole in the needle tube that has penetrated the digestive tract in FIG. 6 is opposed to a cancer cell present outside the digestive tract.

Because the needle tube 2 is made of metal, it is possible to reliably visually confirm the needle tube 2 in an ultrasound image acquired by the ultrasound endoscope 200. An operator confirms the positional relationship between the needle tube 2 and the cancer cell X, in the ultrasound image (Step S7). Specifically, the direction of the opening of the side hole 8 with respect to the cancer cell X is confirmed in the ultrasound image before light emitted from the optical fiber 6 inside the needle tube 2 is radiated onto the cancer cell X, and, as shown in FIG. 7, the near infrared light L from the light source is made to enter the optical fiber 6 when the cancer cell X is located at a position opposed to a radially outer side of the side hole 8 of the needle tube 2.

The near infrared light L that has been made to enter the optical fiber 6 propagates in the core 10 of the optical fiber 6 up to the distal end and is emitted in all radial directions from the emission area A, which is provided at the distal end. Because the emission area A is positioned at the position corresponding to the side hole 8, the near infrared light L emitted from the emission area A passes through the side hole 8 and is radiated onto the cancer cell X located at the radially outer side (Step S8). Accordingly, the drug that has been administered in advance reacts to the near infrared light L to generate heat, thus making it possible to induce death of the cancer cell X.

Specifically, according to the light-irradiation-device delivery apparatus 100 and the phototherapy method of this embodiment, there is an advantage in that it is possible to radiate the near infrared light L onto the cancer cell X, with the emission area A of the optical fiber 6 being accommodated inside the needle tube 2, and to reliably and efficiently radiate the near infrared light L onto the cancer cell X from the emission area A of the optical fiber 6, which has been precisely aligned with the cancer cell X by using an ultrasound image.

Furthermore, in a state in which the distal end of the optical fiber 6 is made to abut against the protrusion 9, thereby positioning the emission area A between the distal end and the proximal end of the side hole 8, the distal end of the optical fiber 6 is completely accommodated in an interior space of the needle tube 2. Specifically, because the optical fiber 6 is not made to protrude from the blade surface 7, which is located at the distal end of the needle tube 2, it is possible to prevent the occurrence of a disadvantageous situation in which an outer surface of the core 10 of the optical fiber 6 is scraped due to sliding between the core 10 and the blade surface 7. Furthermore, if the near infrared light L is emitted in a state in which the core 10 of the optical fiber 6, which is made of resin or glass, is made to protrude from the blade surface 7, it is difficult to visually confirm the core 10 in an ultrasound image; however, according to this embodiment, because it is sufficient to merely confirm the positional relationship between the needle tube 2, which is made of metal, and the cancer cell X, the emission area A can be more reliably aligned with the cancer cell X.

Figure 8:
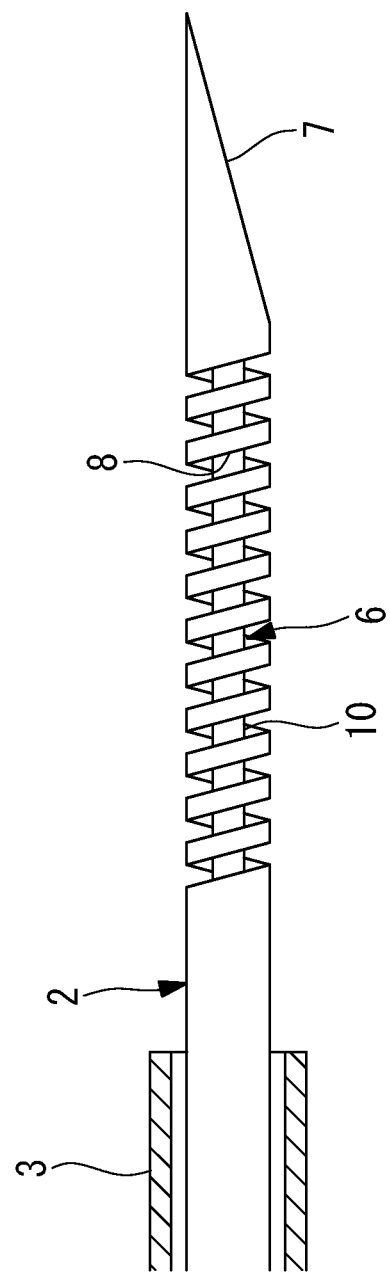
FIG. 8 is a side view showing a modification of the side hole provided in the needle tube shown in FIG. 2.

Furthermore, in this embodiment, although the side hole 8 is formed of a slit that is open, in a circumferential section of the needle tube 2, in a straight line in the longitudinal-axis direction, instead of this, an arbitrary shape may be adopted. For example, as shown in FIG. 8, the side hole 8 may be formed in a spiral shape. In this case, the direction in which the near infrared light L is radiated is not limited to a circumferential section of the needle tube 2 and can be radiated in all radial directions of the needle tube 2.

Figure 9:
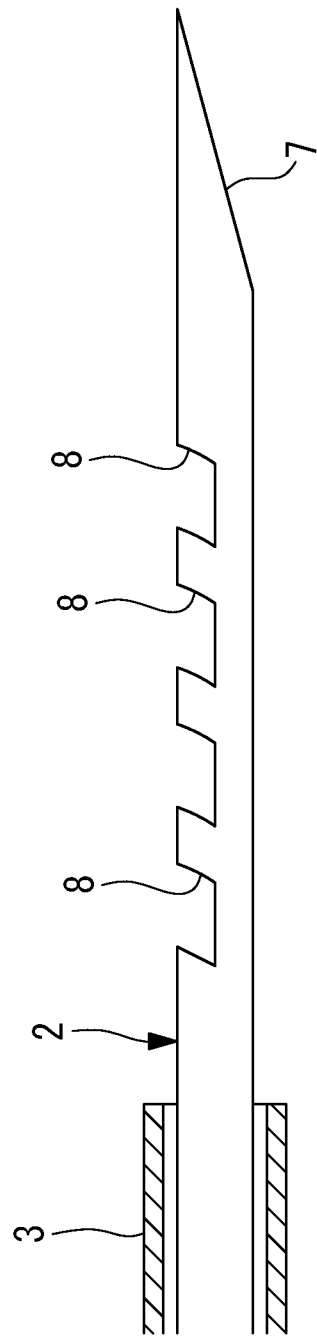
FIG. 9 is a side view showing another modification of the side hole provided in the needle tube shown in FIG. 2.
Figure 10:
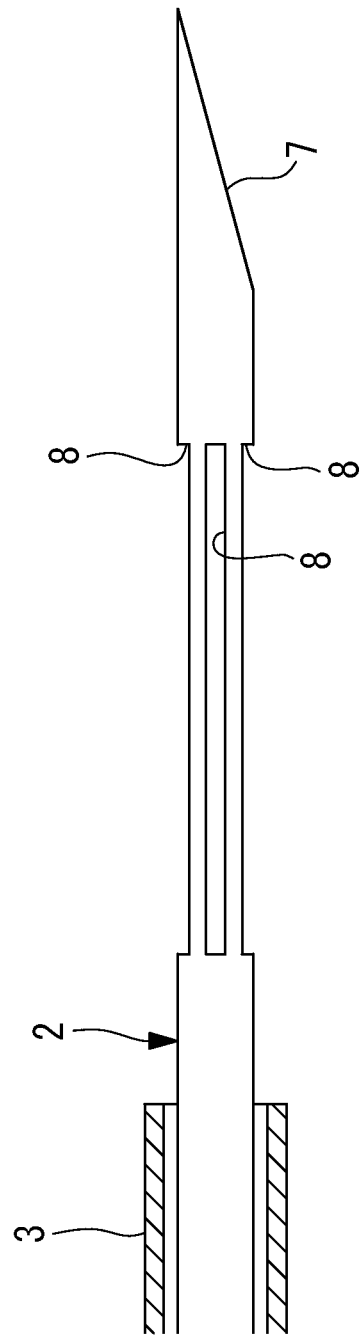
FIG. 10 is a side view showing still another modification of the side hole provided in the needle tube shown in FIG. 2.

Furthermore, the side hole 8 may have a configuration in which a plurality of openings are arranged in the longitudinal-axis direction, as shown in FIG. 9, or may have a configuration in which a plurality of slits that extend and open in the longitudinal-axis direction are arranged in the circumferential direction, as shown in FIG. 10.

Furthermore, although the optical fiber 6 can be prevented from coming out from the side hole 8 by setting the opening width of the side hole 8 so as to be less than the outer diameter of the core 10 of the optical fiber 6, there are cases in which the light intensity of the near infrared light L radiated to the outside of the needle tube 2 is limited.

Figure 11:
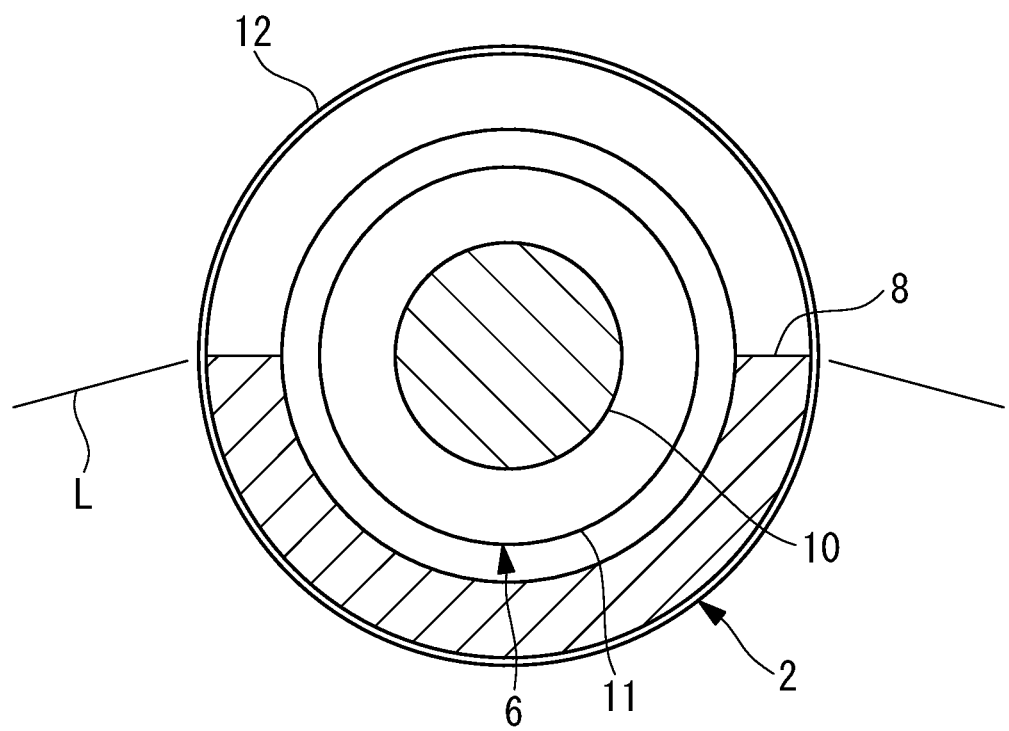
FIG. 11 is a cross-sectional view showing still another modification of the side hole provided in the needle tube shown in FIG. 2.

In contrast to this, as shown in FIG. 11, when the opening width of the side hole 8 is set so as to be greater than the outer diameter of the core 10, and the outside of the side hole 8 is covered with a white, transparent, or translucent film 12, there is an advantage in that a greater amount of the near infrared light L can be radiated onto the cancer cell X in a short time through the side hole 8 that is more widely open, while the film 12 prevents the core 10 from coming out.

Figure 12:
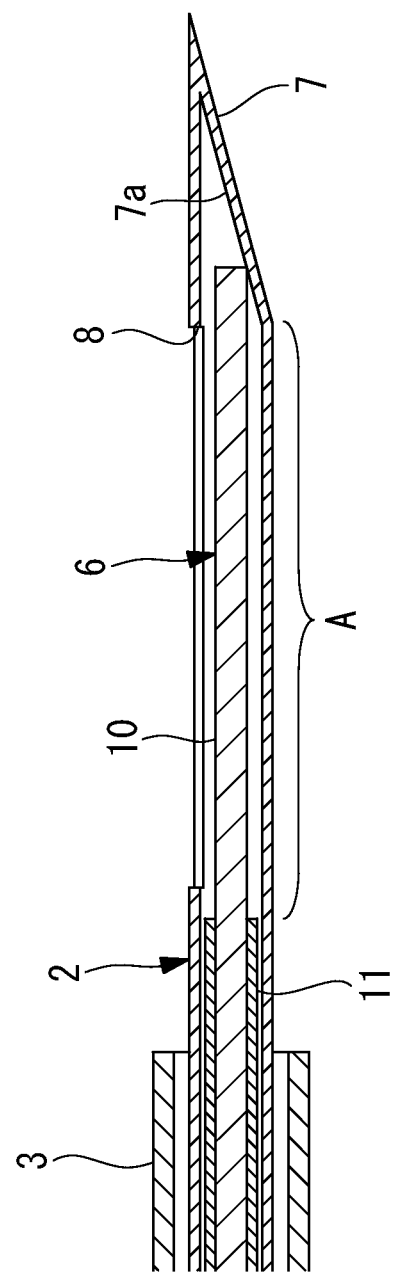
FIG. 12 is a longitudinal sectional view showing a modification of a positioning member in the light-irradiation-device delivery apparatus shown in FIG. 1.

Furthermore, although the protrusion 9, which positions the optical fiber 6 inside the needle tube 2 in the longitudinal-axis direction, is illustrated as the positioning member, instead of this, as shown in FIG. 12, it is also possible to dispose a blocking member 7*a* that blocks the distal end of the needle tube 2 and to position the optical fiber 6 with respect to the needle tube 2 by making the distal end of the optical fiber 6 abut against the blocking member 7*a*.

Figure 13:
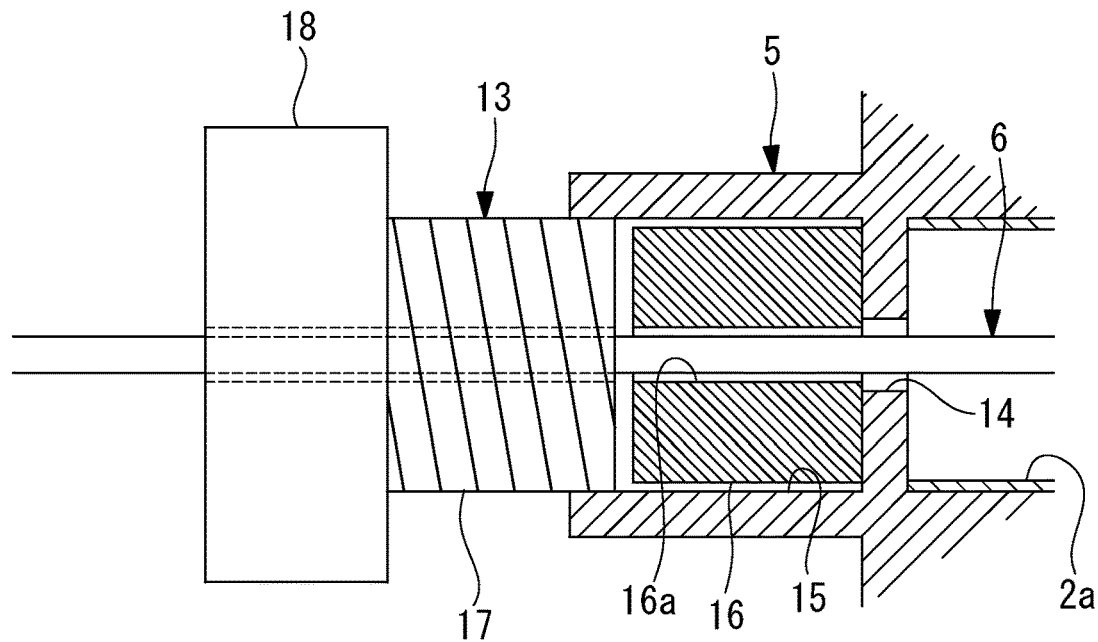
FIG. 13 is a longitudinal sectional view showing an example fixing mechanism that is a modification of the positioning member in the light-irradiation-device delivery apparatus shown in FIG. 1 and that detachably attaches the optical fiber to the needle slider.
Figure 14:
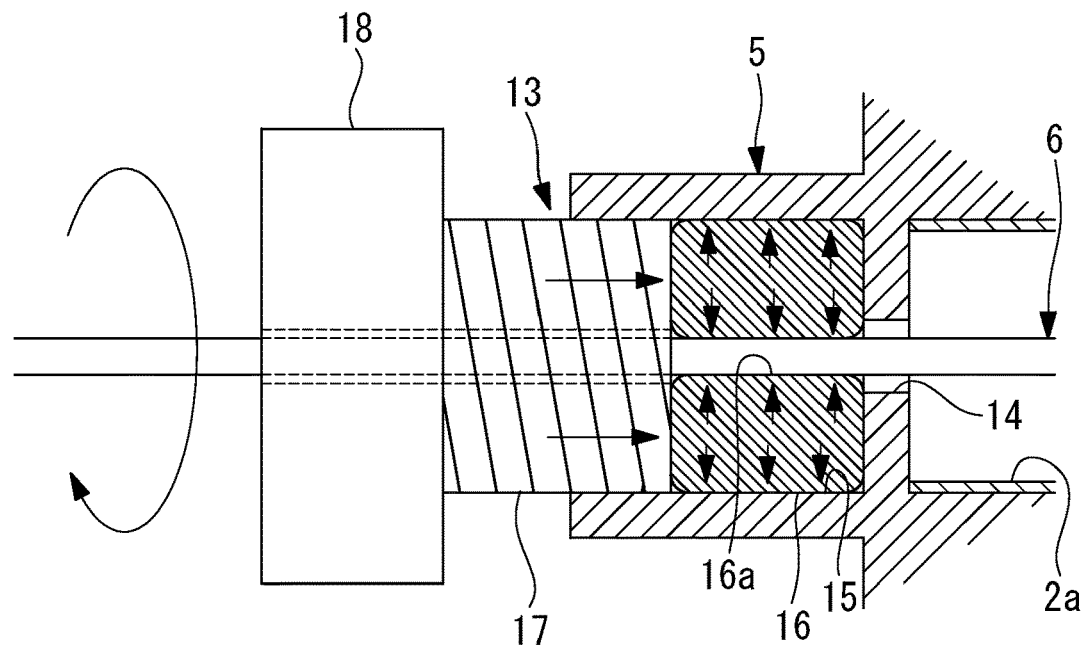
FIG. 14 is a longitudinal sectional view showing a state in which the optical fiber is fixed to the needle slider by the fixing mechanism shown in FIG. 13.
Figure 18:
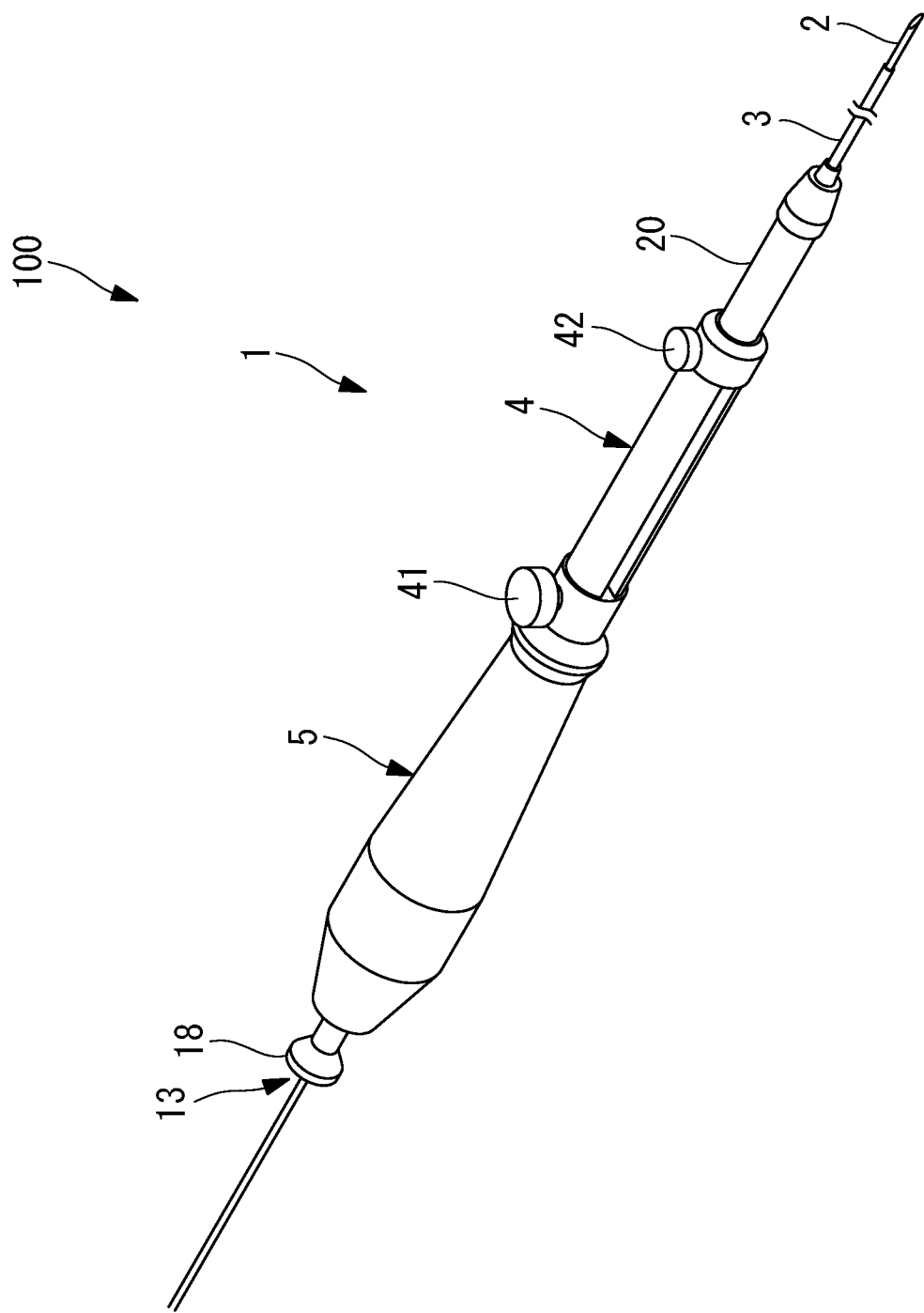
FIG. 18 is a view showing the overall configuration of another modification of the light-irradiation-device delivery apparatus shown in FIG. 1.

Furthermore, in this embodiment, it is also possible to include a fixing mechanism (positioning member) 13 that detachably fixes the optical fiber 6 to the needle slider 5 in a state in which the optical fiber 6 is inserted into the needle tube 2 from the proximal end of the needle tube 2. As shown in FIGS. 13 and 14, for example, the fixing mechanism 13 includes: a screw hole 15 that is provided so as to have a predetermined depth from the proximal end of the needle slider 5 to a proximal end of an insertion hole 14 connected to an inner hole 2*a* of the needle tube 2 and so as to be coaxial with the insertion hole 14 and have a larger diameter than the insertion hole 14; a cylindrical elastic body 16 through which the optical fiber 6 is inserted and that is accommodated in the screw hole 15; a compression member 17 that is fastened into the screw hole 15, thereby compressing the elastic body 16 in the axial direction; and a grip portion 18 that is attached to a proximal end of the compression member 17. As shown in FIG. 18, the grip portion 18 is attached to a proximal end section of the needle slider 5 so as to be easily gripped by the operator. Furthermore, the fixing mechanism 13 may be configured integrally with or separately from the needle slider 5.

When the operator rotates the grip portion 18 to fasten the compression member 17 into the screw hole 15, the elastic body 16 sandwiched between the bottom of the screw hole 15 and the compression member 17 is compressed in the axial direction, thus reducing the inner diameter of a through hole 16*a* of the cylindrical elastic body 16. Accordingly, as shown in FIG. 14, the optical fiber 6, which is inserted through the through hole 16*a*, is tightened radially inward by the elastic body 16, thus making it possible to easily fix the optical fiber 6 to the needle slider 5.

Furthermore, although the protrusion 9, which positions the optical fiber 6 inside the needle tube 2 in the longitudinal-axis direction, is illustrated as the positioning member, instead of this, the positioning member may be formed of only the fixing mechanism 13. Furthermore, the positioning member may be formed by using the fixing mechanism 13, in addition to the protrusion 9 or the blocking member 7*a*.

Figure 15:
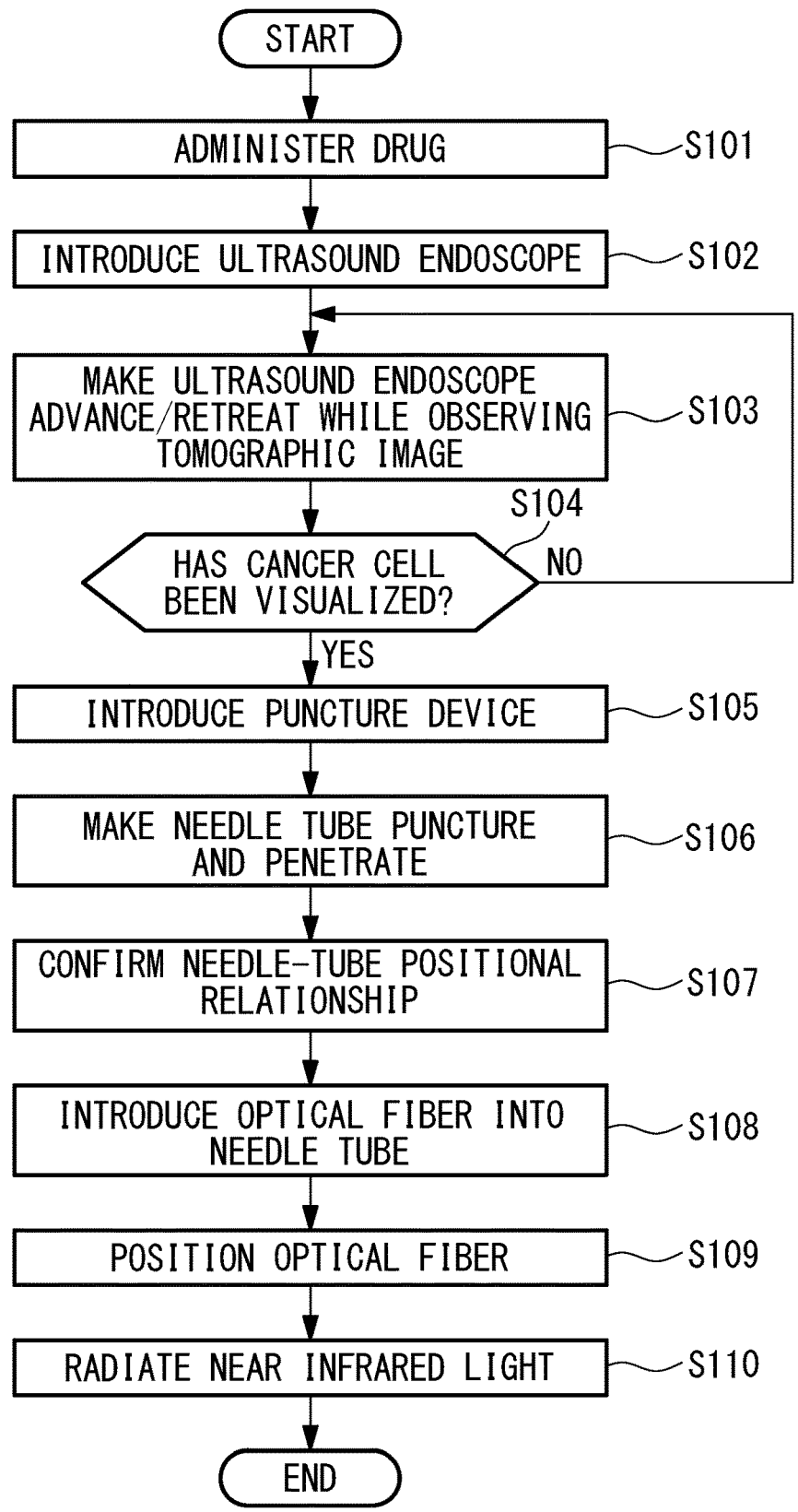
FIG. 15 is a flowchart for explaining the details of the phototherapy method shown in FIG. 5.

Furthermore, in the phototherapy method of this embodiment, more specifically, as shown in FIG. 15, a drug that reacts to the near infrared light L to damage the cancer cell (irradiation target site) X through heat generation etc., thereby inducing cell death of the cancer cell, is administered to a patient in advance (Step S101), and the ultrasound endoscope 200 is introduced into the digestive tract Y such as the stomach or the duodenum (Step S102).

The ultrasound endoscope 200 is made to advance or retreat while observing the cancer cell X present in a tomographic image of the pancreas adjacent to the digestive tract Y by means of the ultrasound endoscope 200 (Step S103), and the ultrasound endoscope 200 is disposed at a position where the cancer cell X can be visualized (Step S104).

When the ultrasound endoscope 200 is inserted up to the position where the cancer cell X can be visualized, the puncture device 1 is made to protrude, via the channel provided in the ultrasound endoscope 200, from the distal end of the channel in the ultrasound endoscope 200 (Step S105). At this time, the attachment adaptor 20 is attached to the channel in the ultrasound endoscope 200. Then, as shown in FIG. 6, the needle tube 2 is made to protrude from the distal-end opening of the channel in the ultrasound endoscope 200, the needle tube 2 punctures the wall of the digestive tract Y, and the needle tube 2 is made to penetrate the wall of the digestive tract Y and punctures the pancreas adjacent to the digestive tract Y (Step S106).

The operator confirms the positional relationship between the needle tube 2 and the cancer cell X, in the ultrasound image (Step S107). Specifically, the direction of the opening of the side hole 8 with respect to the cancer cell X is confirmed in the ultrasound image before light emitted from the optical fiber 6 inside the needle tube 2 is radiated onto the cancer cell X, and the needle tube 2 is stopped when the distal end of the needle tube 2 is disposed in the vicinity of the cancer cell X. Then, the optical fiber 6 is introduced into the needle tube 2 of the puncture device 1 (Step S108) and is positioned by making the distal end of the optical fiber 6 abut against the protrusion 9, which is provided on the inner surface of the needle tube 2 (Step S109). After the cancer cell X is located at a position opposed to a radially outer side of the side hole 8 of the needle tube 2 through the positioning, the near infrared light L from the light source is made to enter the optical fiber 6.

The near infrared light L that has been made to enter the optical fiber 6 propagates in the core 10 of the optical fiber 6 up to the distal end and is emitted in all radial directions from the emission area A, which is provided at the distal end. Because the emission area A is positioned at the position corresponding to the side hole 8, the near infrared light L emitted from the positioned emission area A of the optical fiber 6 passes through the side hole 8 and is radiated onto the cancer cell X located at the radially outer side (Step S110).

Furthermore, although a description has been given of the phototherapy method in which the protrusion 9 is adopted as the positioning member, instead of the protrusion 9, it is also possible to carry out the phototherapy method by using the light-irradiation-device delivery apparatus 100 that adopts the blocking member 7a or the fixing mechanism 13 or to carry out the phototherapy method by using the light-irradiation-device delivery apparatus 100 that adopts: the protrusion 9 or the blocking member 7a; and the fixing mechanism 13.

Figure 16:
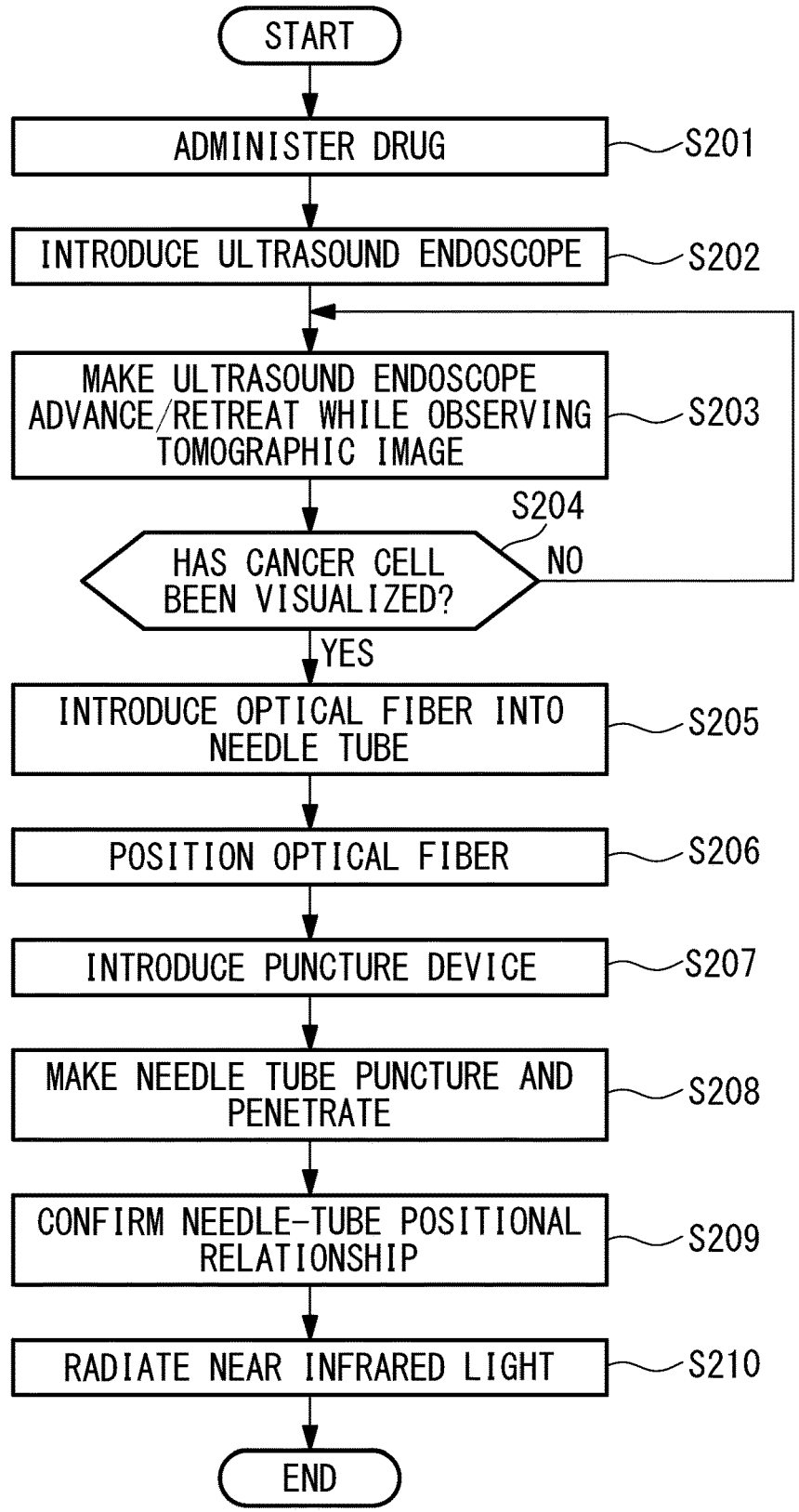
FIG. 16 is a flowchart for explaining a modification of the phototherapy method shown in FIG. 15.

Furthermore, although a description has been given of the method in which, after the positional relationship between the needle tube 2 and the cancer cell X is confirmed (Step S107), and the needle tube 2 is stopped, the optical fiber 6 is introduced into the needle tube 2 (Step S108), instead of this, as shown in FIG. 16, it is also possible to adopt a method in which, after the ultrasound endoscope 200 is moved to a position where the cancer cell X is visualized (Step S204), the optical fiber 6 is introduced into the needle tube 2 (Step S205), and the optical fiber 6 is positioned (Step S206).

Specifically, a drug that reacts to the near infrared light L to damage the cancer cell (irradiation target site) X through heat generation etc., thereby inducing cell death of the cancer cell, is administered to a patient in advance (Step S201), and the ultrasound endoscope 200 is introduced into the digestive tract Y such as the stomach or the duodenum (Step S202).

The ultrasound endoscope 200 is made to advance or retreat while observing the cancer cell X present in a tomographic image of the pancreas adjacent to the digestive tract Y by means of the ultrasound endoscope 200 (Step S203), and the ultrasound endoscope 200 is disposed at a position where the cancer cell X can be visualized (Step S204).

When the ultrasound endoscope 200 is inserted up to the position where the cancer cell X can be visualized, the optical fiber 6 is introduced into the needle tube 2 of the puncture device 1 (Step S205) and is positioned by making the distal end of the optical fiber 6 abut against the protrusion 9, which is provided on the inner surface of the needle tube 2 (Step S206).

Then, the puncture device 1 is made to protrude, via the channel provided in the ultrasound endoscope 200, from the distal end of the channel in the ultrasound endoscope 200 (Step S207). At this time, the attachment adaptor 20 is attached to the channel in the ultrasound endoscope 200. Then, the needle tube 2 is made to protrude from the distal-end opening of the channel in the ultrasound endoscope 200, the needle tube 2 punctures the wall of the digestive tract Y, and the needle tube 2 is made to penetrate the wall of the digestive tract Y and punctures the pancreas adjacent to the digestive tract Y (Step S208).

The operator confirms the positional relationship between the needle tube 2 and the cancer cell X, in the ultrasound image (Step S209). Specifically, the direction of the opening of the side hole 8 with respect to the cancer cell X is confirmed in the ultrasound image before light emitted from the optical fiber 6 inside the needle tube 2 is radiated onto the cancer cell X, and the needle tube 2 is stopped when the distal end of the needle tube 2 is disposed in the vicinity of the cancer cell X. After the cancer cell X is located at a position opposed to a radially outer side of the side hole 8 of the needle tube 2 when the needle tube 2 is stopped, the near infrared light L from the light source is made to enter the optical fiber 6.

The near infrared light L that has been made to enter the optical fiber 6 propagates in the core 10 of the optical fiber 6 up to the distal end and is emitted in all radial directions from the emission area A, which is provided at the distal end. Because the emission area A is positioned at the position corresponding to the side hole 8, the near infrared light L emitted from the positioned emission area A of the optical fiber 6 passes through the side hole 8 and is radiated onto the cancer cell X located at the radially outer side (Step S210).

In this case, although a description has been given of the phototherapy method in which the protrusion 9 is adopted as the positioning member, instead of the protrusion 9, it is also possible to carry out the phototherapy method by using the light-irradiation-device delivery apparatus 100 that adopts the blocking member 7a or the fixing mechanism 13 or to carry out the phototherapy method by using the lightirradiation-device delivery apparatus 100 that adopts: the protrusion 9 or the blocking member 7a; and the fixing mechanism 13.

Figure 17:
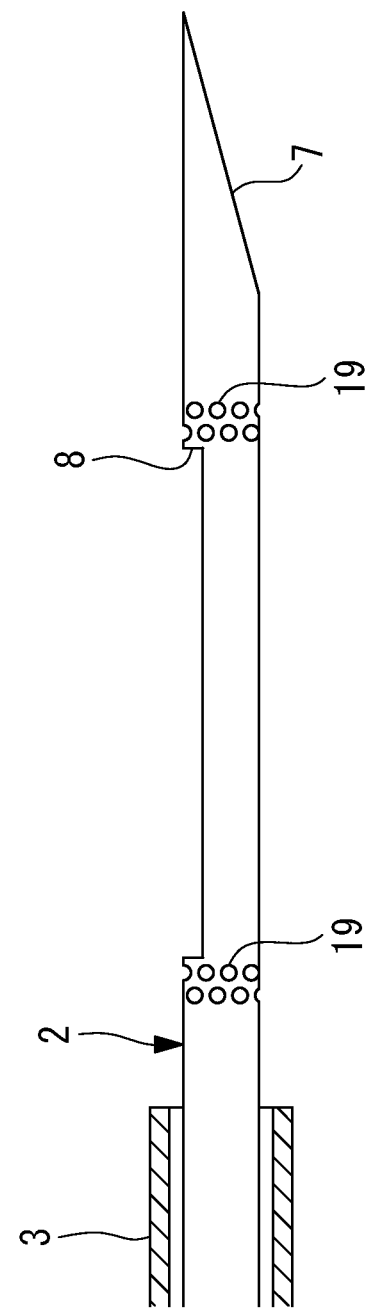
FIG. 17 is a side view showing another modification of the needle tube shown in FIG. 2.

Furthermore, in this embodiment, although the optical fiber 6 is accommodated inside the needle tube 2, which is made of metal, thereby allowing the needle tube 2 to be confirmed in an ultrasound image to align the optical fiber 6 with the cancer cell X, in addition to this, as shown in FIG. 17, the needle tube 2 may have, at two sections that sandwich the side hole 8 in the longitudinal-axis direction, one or more dimples 19 recessed in the outer surface of the needle tube 2.

Because ultrasound is scattered by the dimples 19, the positions of the dimples 19 can be easily visually confirmed in an ultrasound image. Accordingly, there is an advantage in that a section of the needle tube 2 between the two sections where the dimples 19 are provided is aligned with a position opposed to the cancer cell X, thereby making it possible to more effectively radiate the near infrared light L emitted from the side hole 8 onto the cancer cell X.

Furthermore, according to the phototherapy method of this embodiment, when the positional relationship between the needle tube 2 and the cancer cell X is confirmed in the ultrasound image, it is also possible to add a step of rotating the needle tube 2 about the longitudinal axis in accordance with the position of the side hole 8 of the needle tube 2 in the ultrasound image, to adjust the side hole 8 to the position opposed to the cancer cell X.

Furthermore, in this embodiment, although the cancer cell X, such as pancreatic cancer, is illustrated as the irradiation target site, and the near infrared light L is illustrated as light radiated onto the cancer cell X, instead of this, it is also possible to radiate another arbitrary type of light having a therapeutic effect onto another arbitrary irradiation target site.

Furthermore, in the light-irradiation-device delivery apparatus 100 of this embodiment, the outside of the core 10 and the clad 11 of the optical fiber 6 may be covered with a white or transparent protective tube.

Furthermore, in the light-irradiation-device delivery apparatus 100 of this embodiment, although the optical fiber 6 is used, instead of this, an LED, organic electroluminescence, or the like may be used.

Furthermore, in this embodiment, although an example case in which the cancer cell X is present in an organ adjacent to the digestive tract Y is illustrated, instead of this, the present invention may be applied to a case in which the cancer cell X is present in another place, for example, in the wall of the digestive tract Y. In this case, the cancer cell X present in a tomographic image of the wall of the digestive tract Y is confirmed in Step S3, and the needle tube 2 punctures a mucosal surface of the digestive tract Y toward an outer side of the digestive tract Y up to a position in the vicinity of the cancer cell X in the wall of the digestive tract Y, in Step S6. In the other Steps S1, S2, S4, S5, S7, and S8, the same processing is basically carried out.

As a result, the above-described embodiment leads to the following aspects.

One aspect of the present invention is directed to a light-irradiation-device delivery apparatus including: a metal needle tube that has a longitudinal axis and that has a side hole, which penetrates from an inner circumferential surface to an outer circumferential surface, and a blade surface at a distal end thereof; an optical fiber that is accommodated inside the needle tube, that includes a core allowing light to propagate and a clad covering an outer circumferential surface of the core, and that also includes, at a distal-end section thereof, an emission area where the core is exposed by peeling off the clad; and a positioning member that positions the emission area between a distal end and a proximal end of the side hole in the longitudinal-axis direction of the needle tube, wherein the distal end of the optical fiber is positioned in an interior space of the needle tube in a state in which the emission area is positioned between the distal end and the proximal end of the side hole.

According to this aspect, when the optical fiber, which has the emission area where the core is exposed by peeling off the clad at the distal-end section, is accommodated inside the metal tubular needle tube, the optical fiber inside the needle tube is positioned by the positioning member, the emission area is disposed between the distal end and the proximal end of the side hole in the longitudinal-axis direction, the side hole radially penetrating a side wall of the needle tube, and the distal end of the optical fiber is disposed in the interior space.

In this state, the needle tube penetrates tissue, and the needle tube is disposed in the vicinity of an irradiation target site, thereby making it possible to dispose the emission area of the optical fiber in the vicinity of the irradiation target site. Because the needle tube is made of metal, even when the irradiation target site is located outside the digestive tract, it is possible to easily confirm the position of the needle tube by means of the ultrasound endoscope inserted into the digestive tract and to appropriately align the emission area to efficiently radiate emitted light onto the irradiation target site.

In the above-described aspect, the side hole may be open so as to be larger, in the circumferential direction of the needle tube, than an outer-diameter dimension of the core; and the side hole may be covered with a white, transparent, or translucent film.

With this configuration, light emitted from the emission area can be emitted from the side hole, which is largely open, to a wide range at a radially outer side of the needle tube. Because the side hole is covered with the film, the optical fiber can be prevented from falling out from the needle tube via the side hole.

Furthermore, in the above-described aspect, the positioning member may be a protrusion that protrudes, between the blade surface and the distal end of the side hole, radially inward from the inner circumferential surface of the needle tube and against which the distal end of the optical fiber is made to abut.

With this configuration, merely by inserting the optical fiber from the proximal end of the needle tube toward the blade surface, the distal end of the optical fiber is made to abut against the positioning member, thus making it possible to easily dispose the emission area at a position corresponding to the side hole.

Furthermore, the above-described aspect may further include: a sheath that accommodates the needle tube so as to be movable along the longitudinal axis; a main body that is fixed to a proximal end of the sheath; and a needle slider that is supported so as to be movable in the direction along the longitudinal axis with respect to the main body and to which a proximal end of the needle tube is fixed, wherein the needle slider may have the positioning member; the positioning member may be a fixing mechanism that detachably fixes the optical fiber; and the fixing mechanism may include an elastic body that has a through hole through which the optical fiber is inserted and a compression member that compresses the elastic body to constrict the through hole.

With this configuration, the optical fiber is inserted into the needle tube from the proximal end of the needle tube, which is fixed to the needle slider, the optical fiber is fixed to the needle slider by the fixing mechanism, and the needle slider is moved in the direction along the longitudinal axis with respect to the main body, thereby making it possible to make the blade surface of the needle tube advance and retreat.

Furthermore, in a state in which the optical fiber is inserted into the through hole of the elastic body, the compression member compresses the elastic body to constrict the through hole, thereby making it possible to easily fix the optical fiber to the needle slider.

Furthermore, in the above-described aspect, the needle tube may have, at each of sections thereof that sandwich the side hole in the longitudinal-axis direction, one or more dimples recessed in an outer surface.

With this configuration, the position of the side hole in an ultrasound image can be easily confirmed by the dimples, which tend to reflect ultrasound.

Another aspect of the present invention is directed to a phototherapy method including: introducing an ultrasound endoscope into a digestive tract; visualizing an irradiation target site in a body by means of the ultrasound endoscope introduced into the digestive tract; puncturing the vicinity of the irradiation target site with a needle tube made to protrude from a distal-end section of the ultrasound endoscope introduced into the digestive tract; and radiating light emitted from an optical fiber inside the needle tube onto the irradiation target site through a side hole formed in the needle tube that has punctured the vicinity of the irradiation target site.

The above-described aspect may further include inserting the optical fiber into the needle tube after the needle tube that has been made to protrude from the distal-end section of the ultrasound endoscope introduced into the digestive tract punctures the vicinity of the irradiation target site.

Furthermore, the above-described aspect may further include inserting the optical fiber into the needle tube before the needle tube that has been made to protrude from the distal-end section of the ultrasound endoscope introduced into the digestive tract punctures the vicinity of the irradiation target site.

Furthermore, the above-described aspect may further include confirming, in an ultrasound image acquired by the ultrasound endoscope, the direction of an opening of the side hole with respect to the irradiation target site before light emitted from the optical fiber inside the needle tube is radiated onto the irradiation target site.

Furthermore, in the above-described aspect, the confirmation of the positional relationship between the side hole and the irradiation target site may include rotating the needle tube about the longitudinal axis to adjust the direction of the opening of the side hole to a position opposed to the irradiation target site.

Furthermore, in the above-described aspect, the light may be near infrared light; the irradiation target site may be a cancer cell; and the phototherapy method may further include administering a substance that accumulates specifically in the cancer cell and that cause a chemical reaction by being irradiated with the near infrared light, before the ultrasound endoscope is inserted into the digestive tract.

According to the present invention, an advantageous effect is afforded in that an optical fiber is appropriately aligned with a cancer cell, thus making it possible to efficiently radiate emitted light onto the cancer cell.

REFERENCE SIGNS LIST 2 needle tube
4 main body
5 needle slider
6 optical fiber
7 blade surface
7a blocking member (positioning member)
8 side hole
9 protrusion (positioning member)
10 core
11 clad
12 film
13 fixing mechanism (positioning member)
16 elastic body
16a through hole
17 compression member
19 dimple
100 light-irradiation-device delivery apparatus
200 ultrasound endoscope
A emission area
L near infrared light (light)
X cancer cell (irradiation target site)
Y digestive tract

The invention claimed is:

1. A light-irradiation-device delivery apparatus comprising:
   a needle tube extending along a longitudinal axis direction, the needle tube having a blade surface disposed at a distal end of the needle tube and a side hole positioned proximally relative to at least a portion of the blade surface, the side hole penetrating from an inner circumferential surface to an outer circumferential surface;
   an optical fiber comprising a core allowing light to propagate longitudinally and a clad covering an outer circumferential surface of the core,
   the optical fiber being configured to:
     be inserted inside the needle tube;
     move relative to the needle tube in the longitudinal axis direction; and
     emit the light radially from the emission area through the side hole;
   wherein the optical fiber is:
     movable within the needle tube in the longitudinal axis direction in a first state, and
     secured relative to the needle tube in the longitudinal axis direction in a second state such that at least a portion of the emission area radially opposes the side hole.

2. The light-irradiation-device delivery apparatus according to claim 1,
   wherein the side hole having a width in a circumferential direction of the needle tube, the width is larger than an outer-diameter of the core; and
   the side hole is covered with one or more of a white, transparent, or translucent film.

3. The light-irradiation-device delivery apparatus according to claim 1, wherein the needle tube comprises a surface provided between the blade surface and a distal end of the side hole, the surface is configured to prevent the optical fiber from moving distally further than the surface.

4. The light-irradiation-device delivery apparatus according to claim 1, further comprising
   an elastic body,
   wherein the elastic body has a through hole through which the optical fiber is inserted and the elastic body is configured to deform to fix the optical fiber in the second state.

5. The light-irradiation-device delivery apparatus according to claim 1, wherein the needle tube has one or more dimples recessed in the outer circumferential surface to indicate a position of the side hole.

6. The light-irradiation-device delivery apparatus according to claim 1, wherein a distal end of the optical fiber is provided distally relative to a distal end of the side hole when the optical fiber is fixed in the second state.

7. The light-irradiation-device delivery apparatus according to claim 4, further comprising
a compression member,
wherein the compression member is configured to move in the longitudinal axis direction to compress the elastic body.

8. The light-irradiation-device delivery apparatus according to claim 1, wherein the optical fiber comprising:
a first longitudinal portion having the core allowing light to propagate longitudinally and the clad covering the outer circumferential surface of the core; and
a second longitudinal portion being provided distally relative to the first longitudinal portion, the second longitudinal portion having the core without the clad to provide the emission area in which the light radiates radially.

9. The light-irradiation-device delivery apparatus according to claim 1, wherein
the emission area has a first length in the longitudinal axis direction; and
the side hole has a second length in the longitudinal axis direction that is shorter than the first length.

10. The light-irradiation-device delivery apparatus according to claim 1, wherein
the blade surface is inclined relative to a longitudinal axis of the needle tube,
the outer circumferential surface of the needle tube comprises a first outer circumferential surface and a second outer circumferential surface, the first outer circumferential surface has a first length in the longitudinal axis direction longer than a second length in the longitudinal axis direction of the second outer circumferential surface, and
the side hole is provided at the first outer circumferential surface.

11. The light-irradiation-device delivery apparatus according to claim 1, wherein a distal-most end of the optical fiber is positioned in an interior space of the needle tube when at least a portion of the emission area is positioned between a distal end and a proximal end of the side hole, the interior space being enclosed by a circumferential wall of the needle tube and the interior space being distal to the distal end of the side hole.

12. The light-irradiation-device delivery apparatus according to claim 1, wherein the optical fiber is configured to move relative to the needle tube in the longitudinal axis direction without protruding from either a distal hole at the blade surface or the side hole.

13. The light-irradiation-device delivery apparatus according to claim 1, further comprising:
a sheath accommodating the needle tube such that the needle tube is configured to move relative to the sheath in the longitudinal axis direction;
a main body fixed to a proximal end of the sheath; and
a needle slider fixed to a proximal end of the needle tube, and configured to move in the longitudinal axis direction with respect to the main body,
wherein the needle slider comprises a fixing mechanism configured to change between a first state and a second state, wherein the optical fiber is:
movable within the needle tube in the longitudinal axis direction in the first state, and
secured relative to the needle tube in the longitudinal axis direction in the second state such that at least a portion of the emission area radially opposes the side hole.

14. The light-irradiation-device delivery apparatus according to claim 13, wherein the optical fiber is configured to move relative to each of the sheath, the main body and the needle slider.

15. The light-irradiation-device delivery apparatus according to claim 1, wherein the optical fiber is configured to move only linearly along a movable range of the optical fiber in the side hole of the needle tube.

16. The light-irradiation-device delivery apparatus according to claim 1, wherein the side hole has a width in a direction perpendicular to a longitudinal axis direction of the needle tube,
the first longitudinal portion of the optical fiber has an outer diameter, and
the outer diameter is greater than the width.

17. The light-irradiation-device delivery apparatus according to claim 16, wherein the side hole extends along the longitudinal axis direction of the needle tube.

18. The light-irradiation-device delivery apparatus according to claim 1, wherein the needle tube is configured to prevent movement of a distal end the optical fiber longitudinally past a distal end of the needle tube.

19. The light-irradiation-device delivery apparatus according to claim 4, wherein the elastic body is configured to:
in a first state, allow relative movement of the optical fiber relative to the elastic body,
in a second state, fix the optical fiber relative to the elastic body, and
the elastic body has a first length in the longitudinal axis direction in the first state, and has a second length in the longitudinal axis direction in the second state, and
the first length is shorter than the second length.

20. The light-irradiation-device delivery apparatus according to claim 1, wherein the needle tube comprises an inner surface configured to contact with a distal end of the optical fiber to prevent the optical fiber from protruding from a distal end of the needle tube beyond the inner surface of the needle tube.

* * * * *